(12) United States Patent
Niimi et al.

(10) Patent No.: US 8,323,898 B2
(45) Date of Patent: Dec. 4, 2012

(54) METHOD FOR IDENTIFYING PATHOGENIC MICROORGANISMS RESPONSIBLE FOR INFECTION BY EXTRACTING THE DNA OF A MICROORGANISM

(75) Inventors: Hideki Niimi, Fuchu (JP); Isao Kitajima, Fuchu (JP)

(73) Assignee: National University Corporation University of Toyama (JP)

( * ) Notice: Subject to any disclaimer, the term of this patent is extended or adjusted under 35 U.S.C. 154(b) by 213 days.

(21) Appl. No.: 12/194,952

(22) Filed: Aug. 20, 2008

(65) Prior Publication Data

US 2009/0061446 A1 Mar. 5, 2009

Related U.S. Application Data

(63) Continuation of application No. PCT/JP2007/053078, filed on Feb. 20, 2007.

(30) Foreign Application Priority Data

Feb. 21, 2006 (JP) ................................. 2006-043469
Oct. 12, 2006 (JP) ................................. 2006-278371

(51) Int. Cl.
*C12Q 1/68* (2006.01)
*C12P 19/34* (2006.01)
(52) U.S. Cl. ..................................... 435/6.12; 435/91.2
(58) Field of Classification Search .............. 435/6, 91.2
See application file for complete search history.

(56) References Cited

U.S. PATENT DOCUMENTS

| | | | | |
|---|---|---|---|---|
| 5,702,895 | A * | 12/1997 | Matsunaga et al. | 435/6 |
| 6,699,670 | B2 * | 3/2004 | Rothman et al. | 435/6 |
| 6,872,523 | B1 * | 3/2005 | Iwen et al. | 435/6 |
| 7,169,555 | B2 * | 1/2007 | Stuber et al. | 435/6 |
| 2005/0053950 | A1 * | 3/2005 | Zudaire Ubani et al. | 435/6 |

FOREIGN PATENT DOCUMENTS

| | | |
|---|---|---|
| JP | 06-090799 | 4/1994 |
| WO | WO 97/07238 | 2/1997 |
| WO | WO 01/48237 A3 | 7/2001 |
| WO | WO 2004/053148 | 6/2004 |
| WO | WO 2004/053155 | 6/2004 |

OTHER PUBLICATIONS

Lowe et al., Nucleic Acids Research 18(7), 1757-1761 (1990).*
Mori, Mikio, "Real-time PCR kit for sepsis", Journal of Analytical Bio-Science, vol. 28, No. 5, pp. 400-404 (2005).
Tseng Ching-Ping, et al., "Broad-Range Ribosomal RNA Real-Time PCR after Removal of DNA from Reagents: Melting Profiles for Clinically Important Bacteria", XP-002528376, Clinical Chemistry, vol. 49, No. 2, pp. 306-309 (Feb. 2003).
Ririe, Kirk M., et al., "Product Differentiation by Analysis of DNA Melting Curves during the Polymerase Chain Reaction", XP-001015991, Analytical Biochemistry, vol. 245, No. 2, pp. 154-160 (Jan. 1997).
Shepherd, Mervyn, et al., "Monitoring of Fluorescence during DNA Melting as a Method for Discrimination and Detection of PCR Products in Variety Identification", XP-001016033, Molecular Breeding: New Strategies in Plant Improvement, vol. 4, No. 6, pp. 509-517, (Jan. 1998).
Nicolas, Luc, et al., "Rapid Differentiation of Old World *Leishmania* Species by LightCycler Polymerase Chain Reaction and Melting Curve Analysis", XP-002528377, Journal of Microbiological Methods, vol. 51. No. 3, pp. 295-299 (Nov. 2002).
Anthony, R. M., et al., "Rapid Diagnosis of Bacteremia by Universal Amplification of 23S Ribosomal DNA Followed by Hybridization to an Oligonucleotide Array", XP-002176098, Journal of Clinical Microbiology, vol. 38, No. 2, pp. 781-788 (Feb. 2000).
Stranden, A., et al., "Molecular Typing of Methicillin-Resistant *Staphylococcus aureus*: Can PCR Replace Pulsed-Field Gel Electrophoresis?", XP-002419295, Journal of Clinical Microbiology, vol. 41, No. 7, pp. 3181-3186 (Jul. 2003).
Cheng, Ju-Chien, et al., "Rapid Detection and Identification of Clinically Important Bacteria by High-Resolution Melting Analysis after Broad-Range Ribosomal RNA Real-Time PCR", XP-002528378, Clinical Chemistry, vol. 52, No. 11, pp. 1997-2004 (Nov. 2006).

* cited by examiner

*Primary Examiner* — Kenneth R. Horlick
(74) *Attorney, Agent, or Firm* — Harness, Dickey & Pierce, P.L.C.

(57) ABSTRACT

A system rapidly detects and identifies pathogenic bacteria responsible for infection (particularly septicemia), and selects an appropriate antimicrobial drug. A method according to the present invention for detecting and identifying pathogenic bacteria includes performing gene amplification such as real-time PCR, and analyzing the combination of the melting temperatures (Tm values) determined by gene amplification product melting curve analysis or the difference between the Tm values. Specifically, real-time PCR is performed using 4 to 16 primer sets including 1 to 7 primer sets for the 16S ribosomal RNA of bacteria, 1 to 6 primer sets for the 18S ribosomal RNA of fungi, and one primer set respectively for the spa gene and the mecA gene specific to MRSA, and the combination of the Tm values of the amplification product or the combination of the differences between the Tm values is compared with a database to identify pathogenic bacteria responsible for septicemia. Pathogenic bacteria responsible for infection (particularly septicemia) can be rapidly detected and identified using the method according to the invention so that a rapid septicemia diagnosis method and evidence-based medicine in septicemia treatment are implemented.

8 Claims, 1 Drawing Sheet

| ELECTROPHORETIC BAND OF BACTERIA | PRIMER | bac. 6 | fung. 5 | spa. 2 | mecA2 |

| ELECTROPHORETIC BAND OF FUNGI | PRIMER | bac. 6 | fung. 5 | spa. 2 | mecA2 |

| ELECTROPHORETIC BAND OF MRSA | PRIMER | bac. 6 | fung. 5 | spa. 2 | mecA2 |

SEQUENCE LISTING

<160> NUMBER OF SEQ ID NOS: 46

<210> SEQ ID NO 1
<211> LENGTH: 1541
<212> TYPE: DNA
<213> ORGANISM: E.coli

<400> SEQUENCE: 1

```
aaattgaaga gtttgatcat ggctcagatt gaacgctggc ggcaggccta acacatgcaa      60
gtcgaacggt aacaggaaga agcttgctct ttgctgacga gtggcggacg ggtgagtaat     120
gtctgggaaa ctgcctgatg gagggggata actactggaa acggtagcta ataccgcata     180
acgtcgcaag accaaagagg gggacccttcg ggcctcttgc catcggatgt gcccagatgg     240
```
*(Note: "gggacccttcg" may be "ggacccttcg" — reading as shown)*
```
acgtcgcaag accaaagagg gggaccttcg ggcctcttgc catcggatgt gcccagatgg     240
gattagctag taggtggggt aacggctcac ctaggcgacg atccctagct ggtctgagag     300
gatgaccagc cacactggaa ctgagacacg gtccagactc ctacgggagg cagcagtggg     360
gaatattgca caatgggcgc aagcctgatg cagccatgcc gcgtgtatga agaaggcctt     420
cgggttgtaa agtactttca gcggggagga agggagtaaa gttaatacct ttgctcattg     480
acgttacccg cagaagaagc accggctaac tccgtgccag cagccgcggt aatacggagg     540
gtgcaagcgt taatcggaat tactgggcgt aaagcgcacg caggcggttt gttaagtcag     600
atgtgaaatc cccgggctca acctgggaac tgcatctgat actggcaagc ttgagtctcg     660
tagaggggg tagaattcca ggtgtagcgg tgaaatgcgt agagatctgg aggaataccg     720
gtggcgaagg cggccccctg gacgaagact gacgctcagg tgcgaaagcg tggggagcaa     780
acaggattag ataccctggt agtccacgcc gtaaacgatg tcgacttgga ggttgtgccc     840
ttgaggcgtg gcttccggag ctaacgcgtt aagtcgaccg cctggggagt acggccgcaa     900
ggttaaaact caaatgaatt gacggggcc cgcacaagcg gtggagcatg tggtttaatt     960
cgatgcaacg cgaagaacct tacctggtct tgacatccac ggaagttttc agagatgaga    1020
atgtgccttc gggaaccgtg agacaggtgc tgcatggctg tcgtcagctc gtgttgtgaa    1080
atgttgggtt aagtcccgca acgagcgcaa cccttatcct ttgttgccag cggtccggcc    1140
gggaactcaa aggagactgc cagtgataaa ctggaggaag gtgggatga cgtcaagtca    1200
tcatggccct tacgaccagg gctacacacg tgctacaatg gcgcatacaa agagaagcga    1260
cctcgcgaga gcaagcggac ctcataaagt gcgtcgtagt ccggattgga gtctgcaact    1320
cgactccatg aagtcggaat cgctagtaat cgtggatcag aatgccacgg tgaatacgtt    1380
cccgggcctt gtacacaccg cccgtcacac catgggagtg ggttgcaaaa gaagtaggta    1440
gcttaacctt cggagggcg cttaccactt tgtgattcat gactgggtg aagtcgtaac    1500
aaggtaaccg tagggaacc tgcggttgga tcacctcctt a                         1541
```

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2

```
gattagatac cctggtagtc cacg                                              24
```

<210> SEQ ID NO 3
<211> LENGTH: 21
<212> TYPE: DNA

```
<213> ORGANISM: Artificial Sequence
<220> FEATURE:
<223> OTHER INFORMATION: primer

<400> SEQUENCE: 3
cccgtcaatt cctttgagtt t                                          21

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
aaactcaaag gaattgacgg g                                          21

<210> SEQ ID NO 5
<211> LENGTH: 15
<212> TYPE: DNA
<213> ORGANISM: Artificial Sequence
<220> FEATURE:
<223> OTHER INFORMATION: primer

<400> SEQUENCE: 5
cgctcgttgc gggac                                                 15

<210> SEQ ID NO 6
<211> LENGTH: 15
<212> TYPE: DNA
<213> ORGANISM: Artificial Sequence
<220> FEATURE:
<223> OTHER INFORMATION: primer

<400> SEQUENCE: 6
gtcccgcaac gagcg                                                 15

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
attgtagcac gtgtgtagcc c                                          21

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
gggctacaca cgtgctacaa t                                          21

<210> SEQ ID NO 9
<211> LENGTH: 17
<212> TYPE: DNA
<213> ORGANISM: Artificial Sequence
<220> FEATURE:
<223> OTHER INFORMATION: primer

<400> SEQUENCE: 9
ccgggaacgt attcacc                                               17
```

```
<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10
gaatgagtac aatgtaaata ccttaacg                                      28

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
taactgcaac aactttaata tacgc                                         25

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tgaacgaaga acaacgcaat                                               20

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
tttgctcact gaaggatcgt c                                             21

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
attataaagc aatcgctaaa gaactaagta                                    30

<210> SEQ ID NO 15
<211> LENGTH: 26
<212> TYPE: DNA
<213> ORGANISM: Artificial Sequence
<220> FEATURE:
<223> OTHER INFORMATION: primer

<400> SEQUENCE: 15
ccaataactg catcatcttt atagcc                                        26

<210> SEQ ID NO 16
<211> LENGTH: 1788
<212> TYPE: DNA
<213> ORGANISM: C. Albicans

<400> SEQUENCE: 16
```

-continued

| | |
|---|---|
| tatctggttg atcctgccag tagtcatatg cttgtctcaa agattaagcc atgcatgtct | 60 |
| aagtataagc aatttataca gtgaaactgc gaatggctca ttaaatcagt tatcgtttat | 120 |
| ttgatagtac cttactactt ggataaccgt ggtaattcta gagctaatac atgcttaaaa | 180 |
| tcccgactgt ttggaaggga tgtatttatt agataaaaaa tcaatgcctt cgggctcttt | 240 |
| gatgattcat ataacttttt cgaatcgcat ggccttgtgc tggcgatggt tcattcaaat | 300 |
| ttctgcccta tcaactttcg atggtaggat agtggcctac catggtttca acgggtaacg | 360 |
| gggaataagg gttcgattcc ggagagggag cctgagaaac ggctaccaca tccaaggaag | 420 |
| gcagcaggcg cgcaaattac ccaatcccga ttcaggggag gtagtgacaa taaataacga | 480 |
| tacagggccc ttttgggtct tgtaattgga atgagtacaa tgtaaatacc ttaacgagga | 540 |
| acaattggag ggcaagtctg gtgccagcag ccgcggtaat tccagctcca aaagcgtata | 600 |
| ttaaagttgt tgcagttaaa aagctcgtag ttgaactttg ggcttggctg gccggtccat | 660 |
| cttttttcgat gcgtactgga ccagccgagc ctttccttct ggtagccatt tatggcgaac | 720 |
| caggactttt actttgaaaa aattagagtg ttcaaagcag gcctttgctc gaatatatta | 780 |
| gcatggaata atagaatagg acgttatggt tctattgtgt tggtttctag gaccatcgta | 840 |
| atgattaata gggacggtcg ggggtatcag tattcagatg tcgaaggtg aaattcttgg | 900 |
| atttactgaa gactaactac tgcgaaagca tttaccaagg acgttttcat taatcaagaa | 960 |
| cgaaagttag gggatcgaag atgatcagat accgtcgtag tcttaaccat aaactatgcc | 1020 |
| gactagggat cggttgttgt tctttattg acgcaatcgg caccttacga gaaatcaaag | 1080 |
| tctttgggtt ctgggggag tatggtcgca aggctgaaac ttaaaggaat tgacggaagg | 1140 |
| gcaccaccag gagtggagcc tgcggcttaa tttgactcaa cacggggaaa ctcaccaggt | 1200 |
| ccagacacaa taaggattga cagattgaga gctctttctt gattttgtgg gtggtggtgc | 1260 |
| atggccgttc ttagttggtg gagtgatttg tctgcttaat tgcgataacg aacgagacct | 1320 |
| taacctacta aatagtgctg ctagcatttg ctggtatagt cacttcttag agggactatc | 1380 |
| gactccaagt cgatggaagt ttgaggcaat aacaggtctg tgatgccctt agacgttctg | 1440 |
| ggccgcacgc gcgctacact gacggagcca gcgagtataa gccttggccg agaggtctgg | 1500 |
| gaaatcttgt gaaactccgt cgtgctgggg atagagcatt gtaattgttg ctcttcaacg | 1560 |
| aggaattcct agtaagcgca agtcatcagc ttgcgttgat tacgtccctg ccctttgtac | 1620 |
| acaccgcccg tcgctactac cgattgaatg gcttagtgag gcctccggat tggtttagga | 1680 |
| aaggggggcaa ctccattctg gaaccgagaa gctggtcaaa cttggtcatt tagaggaagt | 1740 |
| aaaagtcgta acaaggtttc cgtaggtgaa cctgcggaag gatcatta | 1788 |

```
<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
```

| | |
|---|---|
| agagtttgat catggctcag | 20 |

```
<210> SEQ ID NO 18
<211> LENGTH: 18
<212> TYPE: DNA
<213> ORGANISM: Artificial Sequence
<220> FEATURE:
<223> OTHER INFORMATION: primer
```

```
<400> SEQUENCE: 18
cgtaggagtc tggaccgt                                                18

<210> SEQ ID NO 19
<211> LENGTH: 17
<212> TYPE: DNA
<213> ORGANISM: Artificial Sequence
<220> FEATURE:
<223> OTHER INFORMATION: primer

<400> SEQUENCE: 19
gactcctacg ggaggca                                                 17

<210> SEQ ID NO 20
<211> LENGTH: 17
<212> TYPE: DNA
<213> ORGANISM: Artificial Sequence
<220> FEATURE:
<223> OTHER INFORMATION: primer

<400> SEQUENCE: 20
tattaccgcg gctgctg                                                 17

<210> SEQ ID NO 21
<211> LENGTH: 16
<212> TYPE: DNA
<213> ORGANISM: Artificial Sequence
<220> FEATURE:
<223> OTHER INFORMATION: primer

<400> SEQUENCE: 21
agcagccgcg gtaata                                                  16

<210> SEQ ID NO 22
<211> LENGTH: 23
<212> TYPE: DNA
<213> ORGANISM: Artificial Sequence
<220> FEATURE:
<223> OTHER INFORMATION: primer

<400> SEQUENCE: 22
ggactaccag ggtatctaat cct                                          23

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
aacaggatta gataccctgg tag                                          23

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
aattaaacca catgctccac c                                            21

<210> SEQ ID NO 25
<211> LENGTH: 21
<212> TYPE: DNA
```

```
<213> ORGANISM: Artificial Sequence
<220> FEATURE:
<223> OTHER INFORMATION: primer

<400> SEQUENCE: 25
tggtttaatt cgatgcaacg c                                              21

<210> SEQ ID NO 26
<211> LENGTH: 17
<212> TYPE: DNA
<213> ORGANISM: Artificial Sequence
<220> FEATURE:
<223> OTHER INFORMATION: primer

<400> SEQUENCE: 26
gagctgacga cagccat                                                   17

<210> SEQ ID NO 27
<211> LENGTH: 16
<212> TYPE: DNA
<213> ORGANISM: Artificial Sequence
<220> FEATURE:
<223> OTHER INFORMATION: primer

<400> SEQUENCE: 27
ttgggttaag tcccgc                                                    16

<210> SEQ ID NO 28
<211> LENGTH: 16
<212> TYPE: DNA
<213> ORGANISM: Artificial Sequence
<220> FEATURE:
<223> OTHER INFORMATION: primer

<400> SEQUENCE: 28
cgtcatcccc accttc                                                    16

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
ggctacacac gtgctacaat                                                20

<210> SEQ ID NO 30
<211> LENGTH: 17
<212> TYPE: DNA
<213> ORGANISM: Artificial Sequence
<220> FEATURE:
<223> OTHER INFORMATION: primer

<400> SEQUENCE: 30
ccgggaacgt attcacc                                                   17

<210> SEQ ID NO 31
<211> LENGTH: 26
<212> TYPE: DNA
<213> ORGANISM: Artificial Sequence
<220> FEATURE:
<223> OTHER INFORMATION: primer

<400> SEQUENCE: 31
gtggtaattc tagagctaat acatgc                                         26
```

<210> SEQ ID NO 32
<211> LENGTH: 17
<212> TYPE: DNA
<213> ORGANISM: Artificial Sequence
<220> FEATURE:
<223> OTHER INFORMATION: primer

<400> SEQUENCE: 32
ggtagccgtt tctcagg                                               17

<210> SEQ ID NO 33
<211> LENGTH: 19
<212> TYPE: DNA
<213> ORGANISM: Artificial Sequence
<220> FEATURE:
<223> OTHER INFORMATION: primer

<400> SEQUENCE: 33
gcctgagaaa cggctacca                                             19

<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
cctccaattg ttcctcgtta ag                                         22

<210> SEQ ID NO 35
<211> LENGTH: 22
<212> TYPE: DNA
<213> ORGANISM: Artificial Sequence
<220> FEATURE:
<223> OTHER INFORMATION: primer

<400> SEQUENCE: 35
ttaacgagga acaattggag gg                                         22

<210> SEQ ID NO 36
<211> LENGTH: 23
<212> TYPE: DNA
<213> ORGANISM: Artificial Sequence
<220> FEATURE:
<223> OTHER INFORMATION: primer

<400> SEQUENCE: 36
gcctgctttg aacactctaa ttt                                        23

<210> SEQ ID NO 37
<211> LENGTH: 21
<212> TYPE: DNA
<213> ORGANISM: Artificial Sequence
<220> FEATURE:
<223> OTHER INFORMATION: primer

<400> SEQUENCE: 37
ataccgtcgt agtcttaacc a                                          21

<210> SEQ ID NO 38
<211> LENGTH: 24
<212> TYPE: DNA
<213> ORGANISM: Artificial Sequence
<220> FEATURE:
<223> OTHER INFORMATION: primer

```
<400> SEQUENCE: 38
gtcaattcct ttaagtttca gcct                                          24

<210> SEQ ID NO 39
<211> LENGTH: 19
<212> TYPE: DNA
<213> ORGANISM: Artificial Sequence
<220> FEATURE:
<223> OTHER INFORMATION: primer

<400> SEQUENCE: 39
catggccgtt cttagttgg                                                19

<210> SEQ ID NO 40
<211> LENGTH: 18
<212> TYPE: DNA
<213> ORGANISM: Artificial Sequence
<220> FEATURE:
<223> OTHER INFORMATION: primer

<400> SEQUENCE: 40
gggcatcaca gacctgtt                                                 18

<210> SEQ ID NO 41
<211> LENGTH: 19
<212> TYPE: DNA
<213> ORGANISM: Artificial Sequence
<220> FEATURE:
<223> OTHER INFORMATION: primer

<400> SEQUENCE: 41
aggtctgtga tgcccttag                                                19

<210> SEQ ID NO 42
<211> LENGTH: 17
<212> TYPE: DNA
<213> ORGANISM: Artificial Sequence
<220> FEATURE:
<223> OTHER INFORMATION: primer

<400> SEQUENCE: 42
cgggcggtgt gtacaaa                                                  17

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
taaacgatgc tcaagcacca a                                             21

<210> SEQ ID NO 44
<211> LENGTH: 21
<212> TYPE: DNA
<213> ORGANISM: Artificial Sequence
<220> FEATURE:
<223> OTHER INFORMATION: primer

<400> SEQUENCE: 44
ggtttaacga catgtactcc g                                             21

<210> SEQ ID NO 45
<211> LENGTH: 23
<212> TYPE: DNA
```

```
<213> ORGANISM: Artificial Sequence
<220> FEATURE:
<223> OTHER INFORMATION: primer

<400> SEQUENCE: 45
caaactacgg taacattgat cgc                                              23

<210> SEQ ID NO 46
<211> LENGTH: 22
<212> TYPE: DNA
<213> ORGANISM: Artificial Sequence
<220> FEATURE:
<223> OTHER INFORMATION: primer

<400> SEQUENCE: 46
atgtatgctt tggtctttct gc                                               22
```

METHOD FOR IDENTIFYING PATHOGENIC MICROORGANISMS RESPONSIBLE FOR INFECTION BY EXTRACTING THE DNA OF A MICROORGANISM

CROSS REFERENCE TO RELATED APPLICATION

This application is a continuation of International Patent Application No. PCT/JP2007/053078, having an international filing date of Feb. 20, 2007, which designated the United States, the entirety of which is incorporated herein by reference. Japanese Patent Application No. 2006-043469 filed on Feb. 21, 2006 and Japanese Patent Application No. 2006-278371 filed on Oct. 12, 2006 are also incorporated herein by reference in their entirety.

BACKGROUND

The present invention relates to a method for quickly detecting and identifying pathogenic bacteria in order to treat an infection (particularly septicemia) at an early stage.

Septicemia is a serious systemic infection. It is indispensable to detect and identify pathogenic bacteria in blood for definite diagnosis of septicemia.

In recent years, the number of serious patients who are likely to develop septicemia has increased with the advancement of medical treatment such as cancer therapy and an organ transplant.

Multi-drug resistant bacteria such as *methicillia* resistant *staphlococcus aureus* (MRSA) may cause septicemia from the viewpoint of nosocomial infection. In order to select an appropriate antimicrobial drug to save the life of the patient, it is important to detect and identify pathogenic bacteria in blood as promptly as possible in clinical practice.

However, since the current microbiological detection method takes at least 18 hours to identify bacteria after submission of a blood culture bottle, it is necessary to carry out empirical therapy until the result is obtained. Therefore, the antimicrobial drug has been necessarily selected blindly.

As a result, multi-drug resistant bacteria may emerge due to the use of a broad-spectrum antimicrobial drug, or a situation in which the life of the septic patient cannot be saved due to inappropriate selection of the antimicrobial drug may occur.

A method that amplifies the DNA of pathogenic bacteria responsible for septicemia by polymerase chain reaction (PCR), and hybridizes the amplified DNA of the pathogenic bacteria with a nucleotide probe specific to the target bacterial species empirically determined to detect and identify the pathogenic bacteria has been disclosed (JP-A-6-90799).

Real-time PCR technology has also been developed in order to achieve prompt detection and identification (Journal of Analytical Bio-Science, Vol. 28, No. 5. (2005), pp. 400 to 404).

The basic principle of this septicemia examination method is real-time PCR using a hybridization probe.

However, it is necessary to prepare a hybridization probe specific to each bacterial species when using this method. Therefore, in order to identify a large number of pathogenic bacteria, it is necessary to prepare a large number of hybridization probes.

Specifically, since the number of bacterial species to be detected is determined by the number of probes to be prepared, it is practically impossible to identify a wide range of bacterial species.

SUMMARY

The inventors of the invention conducted extensive studies on application of the difference in melting temperature (Tm value) between bacterial species to identify pathogenic bacteria based on the theoretical concept that the Tm value is determined by the base sequence in the nearest neighbor method to complete the invention.

The invention provides a method for quickly detecting and identifying pathogenic bacteria comprising extracting the DNA of a microorganism, subjecting the DNA as a template to gene amplification by PCR or the like using a specific primer set, and analyzing the combination of the melting temperatures (Tm values) specific to the microorganism or the difference between the Tm values.

DESCRIPTION OF EXEMPLARY EMBODIMENTS

The invention is described in detail below.
(1) It is known that the 16S rRNA of bacteria has seven or eight base sequence regions (20 to 40 bases) common to almost all bacteria.
  A forward primer and a reverse primer are respectively set for all or some of these base sequence regions to prepare one to seven gene amplification regions.
(2) The gene amplification region contains about 150 to 200 bases. The base sequence specific to each bacterium remains excluding the common conservation regions for which the primers are set.
  Therefore, the Tm value specific to each bacterium is obtained due to the difference in base sequence. It is estimated that each bacterium has one to seven specific Tm values.
  Therefore, one to seven Tm values corresponding to each type of bacteria are determined and stored in a database.
  Unknown bacteria can be identified by utilizing the database.
(3) A bacterial infection and its type (including MRSA) or a fungal infection and its type can be identified using one to six primers specific to fungi, spa and mecA primers for MRSA identification in combination for unknown pathogenic bacteria.
(4) When a non-specific gene product is produced and shows a Tm value close to the desired Tm value, a false positive result may be obtained.
  In this case, the product obtained by gene amplification is placed in an agarose gel, and the band is determined to double-check the result.
  Specifically, the examination accuracy can be increased by employing a double-check system utilizing a known gene amplification detection method.
(5) When employing real-time PCR as the gene amplification method, the amount of bacteria can be relatively determined before and after the treatment utilizing the quantitative nature of real-time PCR so that the therapeutic effect can be monitored in an improved manner.
(6) A real-time PCR instrument is classified as a heating-block real-time PCR instrument that controls the temperature using a heating block and an air-bath instrument that controls the temperature utilizing air. A Tm value measurement error of +0.1 to 0.3° C. occurs when using a heating-block real-time PCR instrument (depending on the manufacturer), and a Tm value measurement error of +0.4 occurs when using an air-bath real-time PCR instrument corresponding to each measurement cycle.

It is preferable to employ a method that utilizes a differential pattern between Tm values obtained by the same measurement cycle for the determination so that bacterial species identification is not hindered due to measurement error.

The primers used in the invention are as follows.

Combination group 1

Five sequence sites are selected from the sequence sites common to the 16S rRNA genes of all bacteria, and a forward primer and a reverse primer are set for each site.

Specifically, primers including all or some of the following base sequences are used.

(B1) Primer set that amplifies DNA containing 97 bases corresponding to the 809th to 905th bases of the 16S rRNA gene of Escherichia coli (E. coli) (Sequence ID No. 1) (bacteria primer 1: Bac.1)

Sequence ID No. 2: GATTAGATACCCTGGTAGTCCACG (24 mer) forward

Sequence ID No. 3: CCCGTCAATTCCTTTGAGTTT (21 mer) reverse (B2) Primer set that amplifies DNA containing 166 bases corresponding to the 927th to 1092nd bases of the 16S rRNA gene of E. coli (bacteria primer 2: Bac.2)

Sequence ID No. 4: AAACTCAAAGGAATTGACGGG (21 mer) forward

Sequence ID No. 5: CGCTCGTTGCGGGAC (15 mer) reverse (B3) Primer set that amplifies DNA containing 111 bases corresponding to the 1108th to 1218th bases of the 16S rRNA gene of E. coli (bacteria primer 3: Bac.3)

Sequence ID No. 6: GTCCCGCAACGAGCG (15 mer) forward

Sequence ID No. 7: ATTGTAGCACGTGTGTAGCCC (21 mer) reverse (B4) Primer set that amplifies DNA containing 130 bases corresponding to the 1240th to 1369th bases of the 16S rRNA gene of E. coli (bacteria primer 4: Bac.4)

Sequence ID No. 8: GGGCTACACACGTGCTACAAT (21 mer) forward

Sequence ID No. 9: CCGGGAACGTATTCACC (17 mer) reverse

A sequence region common to the 18S rRNA genes of all fungi is selected, and a forward primer and a reverse primer are set.

Specifically, primers including all or some of the following base sequences are used.

(F1) Primer set for the 18S rRNA gene of fungi (fungi primer: Fungi)

Sequence ID No. 10: GAATGAGTACAATGTAAATACCTTAACG (28 mer) forward

Sequence ID No. 11: TAACTGCAACAACTTTAATATACGC (25 mer) reverse

Regarding primers for the Spa gene and the mecA gene of MRSA, a primer design with the highest score is selected using the LightCycler Probe Design2 software.

(M1) Primer set for the Spa gene of MRSA (spa primer: spa)

Sequence ID No. 12: TGAACGAAGAACAACGCAAT (20 mer) forward

Sequence ID No. 13: TTTGCTCACTGAAGGATCGTC (21 mer) reverse (M2) Primer set of the mecA gene of MRSA (mecA primer: mecA)

Sequence ID No. 14: ATTATAAAGCAATCGCTAAAGAACTAAGTA (30 mer) forward

Sequence ID No. 15: CCAATAACTGCATCATCTTTATAGCC (26 mer) reverse Combination group 2

Ten sequence sites are selected from the sequence sites common to the 16S rRNA genes of all bacteria, and a forward primer and a reverse primer are set for each site.

Specifically, primers including all or some of the following base sequences are used.

(B5) Primer set that amplifies DNA containing 338 bases corresponding to the 8th to 345th bases of the 16S rRNA gene of E. coli (bacteria primer 5: Bac.5)

Sequence ID No. 17: AGAGTTTGATCATGGCTCAG (20 mer) forward

Sequence ID No. 18: CGTAGGAGTCTGGACCGT (18 mer) reverse (B6) Primer set that amplifies DNA containing 199 bases corresponding to the 336th to 534th bases of the 16S rRNA gene of E. coli (bacteria primer 6: Bac.6)

Sequence ID No. 19: GACTCCTACGGGAGGCA (17 mer) forward

Sequence ID No. 20: TATTACCGCGGCTGCTG (17 mer) reverse (B7) Primer set that amplifies DNA containing 287 bases corresponding to the 519th to 805th bases of the 16S rRNA gene of E. coli (bacteria primer 7: Bac.7)

Sequence ID No. 21: AGCAGCCGCGGTAATA (16 mer) forward

Sequence ID No. 22: GGACTACCAGGGTATCTAATCCT (23 mer) reverse (B8) Primer set that amplifies DNA containing 181 bases corresponding to the 780th to 960th bases of the 16S rRNA gene of E. coli (bacteria primer 8: Bac.8)

Sequence ID No. 23: AACAGGATTAGATACCCTGGTAG (23 mer) forward

Sequence ID No. 24: AATTAAACCACATGCTCCACC (21 mer) reverse (B9) Primer set that amplifies DNA containing 120 bases corresponding to the 951st to 1070th bases of the 16S rRNA gene of E. coli (bacteria primer 9: Bac.9)

Sequence ID No. 25: TGGTTTAATTCGATGCAACGC (21 mer) forward

Sequence ID No. 26: GAGCTGACGACAGCCAT (17 mer) reverse (B10) Primer set that amplifies DNA containing 109 bases corresponding to the 1084th to 1192nd bases of the 16S rRNA gene of E. coli (bacteria primer 10: Bac.10)

Sequence ID No. 27: TTGGGTTAAGTCCCGC (16 mer) forward

Sequence ID No. 28: CGTCATCCCCACCTTC (16 mer) reverse (B11) Primer set that amplifies DNA containing 166 bases corresponding to the 1220th to 1385th bases of the 16S rRNA gene of E. coli (bacteria primer 11: Bac.11)

Sequence ID No. 29: GGCTACACACGTGCTACAAT (20 mer) forward

Sequence ID No. 30: CCGGGAACGTATTCACC (17 mer) reverse

Seven sequence sites are selected from the sequence sites common to the 18S rRNA genes of fungi, and a forward primer and a reverse primer are set for each site.

Specifically, primers including all or some of the following base sequences are used.

(F2) Primer set that amplifies DNA containing 259 bases corresponding to the 149th to 407th bases of the 18S rRNA gene of C. Albicans (Sequence ID No. 16) (fungi primer 2: Fungi 2)

Sequence ID No. 31: GTGGTAATTCTAGAGCTAATACATGC (26 mer) forward

Sequence ID No. 32: GGTAGCCGTTTCTCAGG (17 mer) reverse (F3) Primer set that amplifies DNA containing 162 bases corresponding to the 390th to 551st bases of the 18S rRNA gene of *C. Albicans* (fungi primer 3: Fungi 3)
Sequence ID No. 33: GCCTGAGAAACGGCTACCA (19 mer) forward
Sequence ID No. 34: CCTCCAATTGTTCCTCGTTAAG (22 mer) reverse
(F4) Primer set that amplifies DNA containing 232 bases corresponding to the 531st to 762nd bases of the 18S rRNA gene of *C. Albicans* (fungi primer 4: Fungi 4)
Sequence ID No. 35: TTAACGAGGAACAATTGGAGGG (22 mer) forward
Sequence ID No. 36: GCCTGCTTTGAACACTCTAATTT (23 mer) reverse
(F5) Primer set that amplifies DNA containing 146 bases corresponding to the 989th to 1134th bases of the 18S rRNA gene of *C. Albicans* (fungi primer 5: Fungi 5)
Sequence ID No. 37: ATACCGTCGTAGTCTTAACCA (21 mer) forward
Sequence ID No. 38: GTCAATTCCTTTAAGTTTCAGCCT (24 mer) reverse
(F6) Primer set that amplifies DNA containing 169 bases corresponding to the 1260th to 1428th bases of the 18S rRNA gene of *C. Albicans* (fungi primer 6: Fungi 6)
Sequence ID No. 39: CATGGCCGTTCTTAGTTGG (19 mer) forward
Sequence ID No. 40: GGGCATCACAGACCTGTT (18 mer) reverse
(F7) Primer set that amplifies DNA containing 217 bases corresponding to the 1414th to 1630th bases of the 18S rRNA gene of *C. Albicans* (fungi primer 7: Fungi 7)
Sequence ID No. 41: AGGTCTGTGATGCCCTTAG (19 mer) forward
Sequence ID No. 42: CGGGCGGTGTGTACAAA (17 mer) reverse Regarding primers for the Spa gene and the mecA gene of MRSA, a primer design with the highest score is selected using the LightCycler Probe Design2 software.
(M3) Primer set for the Spa gene of MRSA (spa primer 2: spa2)
Sequence ID No. 43: TAAACGATGCTCAAGCACCAA (21 mer) forward
Sequence ID No. 44: GGTTTAACGACATGTACTCCG (21 mer) reverse
(M4) Primer set for the mecA gene of MRSA (mecA primer 2: mecA2)
Sequence ID No. 45: CAAACTACGGTAACATTGATCGC (23 mer) forward
Sequence ID No. 46: ATGTATGCTTTGGTCTTTCTGC (22 mer) reverse As the gene amplification method according to the invention, PCR is preferable, with real-time PCR being more preferable.

Real-time PCR used in the invention is an intercalator method that adds an intercalator that emits fluorescence upon binding to a double-stranded DNA to the PCR reaction system.

Examples of the intercalator include ethidium bromide, SYBR Green I, and the like.

SYBR Green I is preferable as the intercalator.

Since the primer used in the invention reacts with the DNA of all bacteria, it is necessary to use high-purity SYBR Green I in which mixing of the DNA of bacteria originating from the recombinant host is minimized.

In the invention, the term "Tm value" refers to a temperature when 50% of the PCR product dissociates from the complementary strand.

The difference in base sequence between bacterial species can be applied to identify pathogenic bacteria as the difference in Tm value between bacterial species based on the theoretical concept that the Tm value is determined by the base sequence in the nearest neighbor method (Tm value formula).

Therefore, it is most important to eliminate the effect of a measurement error from the Tm value in order to achieve accurate identification. The effect of a measurement error is eliminated by the following method.

Specifically, since the Tm value changes under experimental conditions that differ in the composition of a buffer and the like, a measurement error due to the composition of the reaction liquid is prevented by utilizing SYBR Green I with a specific magnesium chloride concentration as the reaction buffer.

Since the real-time PCR instrument produces a measurement error corresponding to each measurement cycle, a reference Tm value is set as control, and the differential pattern between the Tm values obtained in the same measurement cycle is utilized for the determination.

In the invention, the reference Tm value can be used to correct a cycle-to-cycle error of the measurement instrument.

Specifically, the DNA of an *E. coli* standard strain with a constant concentration is used as the template. The Tm value is measured using one primer set that amplifies one region of the 16S rRNA gene of bacteria, and an error in Tm value corresponding to each measurement cycle is corrected.

Specifically, when an identical template and an identical primer are used, an identical Tm value is theoretically obtained in each measurement cycle.

If the measured Tm value has changed (cycle-to-cycle error), the Tm value is corrected corresponding to the error.

The process of the method according to the invention is as follows.

(1) The DNA of a microorganism is extracted.
(2) The extracted DNA of the unknown microorganism is subjected to gene amplification using the primer set for bacteria, MRSA, and fungi. The Tm values are then measured at a time to obtain the combination of the Tm values for bacteria, MRSA, and fungi.
(3) Whether or not the microorganism is a fungus is determined.

Specifically, whether or not the microorganism is a fungus or the fungus type is determined by analyzing the Tm value specific to fungi obtained using the primer set that can amplify one region to a plurality of regions of the 18S rRNA genes of all fungi among the Tm values obtained in (2).

(4) Whether or not the microorganism is MRSA is determined.

Specifically, whether or not the microorganism is MRSA is determined by analyzing gene amplification specific to MRSA obtained using the primer set that specifically amplifies the Spa gene and the mecA gene of MRSA among the Tm values obtained in (2).

(5) The range of the bacterial species is narrowed.

The bacterial species is determined by analyzing the Tm value specific to bacteria obtained using the primer set that can amplify a plurality of regions of the 16S rRNA genes of all bacteria among the Tm values obtained in (2).

Specifically, one of the Tm values specific to bacteria is selected (the Tm value may be corrected using the reference Tm value). The range of the bacterial species is narrowed to bacterial species having a value close to the Tm value. The difference in Tm value is sequentially calculated to narrow the range, or the difference in Tm value including the reference Tm value is directly calculated, and the bacterial species is identified using the combination of the differences as a fingerprint.

As a method that promptly and conveniently determines whether the pathogenic bacteria are bacteria, fungi, or MRSA, a method may be used that extracts the DNA of an unknown microorganism, subjects the extracted DNA as a template to PCR using (1) one primer that is common to the 18S rRNA genes of all fungi and specifically detects fungi, (2) two primers that specifically detect the Spa gene and the mecA gene of MRSA, respectively, and (3) one primer that is common to the 16S rRNA genes of all bacteria and specifically detects bacteria, and performs agarose gel electrophoresis to determine the band with a desired size.

(1) The bacterial species of pathogenic bacteria necessary for antimicrobial drug selection can be identified by performing gene amplification such as real-time PCR based on 4 to 18, and preferably 4 to 16 primer sets, and comparing the resulting Tm values with the database.
(2) When the sample is blood, the time required for DNA extraction, Tm value analysis, and identification is about two hours. Therefore, rapid diagnosis becomes possible.
(3) When the amount of blood sample from which DNA is extracted is constant, the relative amount of bacteria can be determined. This makes it possible to monitor the therapeutic effects after administration of the antimicrobial drug.

factured by Nissui Pharmaceutical Co., Ltd.), and Sabouraud's agar (manufactured by Nippon Becton Dickinson Company, Ltd.). After suspending one colony in a microtube containing 1 ml of sterilized saline, the mixture was centrifuged at 12,000 rpm for two minutes. After removing the supernatant liquid, 200 μl of Insta Gene Matrix (manufactured by Bio-Rad Laboratories, Inc.) was added to the bacterial pellets. The mixture was heated at 56° C. for 15 to 30 minutes.

The microtube was then intensely vortexed, and boiled for eight minutes using a heating block at 100° C.

The mixture was then centrifuged at 12,000 rpm for two minutes. The supernatant liquid was used as a DNA extract.
Real-Time PCR A real-time PCR instrument "LightCycler 1.5" (manufactured by Roche Diagnostics K.K.) was used.

An intercalator "Power SYBR Green PCR Master Mix" (manufactured by Applied Biosystems) was used as a real-time PCR intercalator.

The PCR system (20 μl) contained 2 μl of the genomic DNA template, 2 μl of the ten-fold concentrated PCR primer (final concentration: 250 nM), 10 μl of the ten-fold concentrated real-time PCR intercalator, 2 μl of BSA (500 μg/ml), and 4 μl of ultrapure water.

Table 1 shows the real-time PCR program setting.

The elongation time was set at 12 seconds which was the minimum time enabling amplification up to a 300-base length.

Table 1 shows the real-time PCR program setting.

TABLE 1

| Program | Analysis mode | Number of cycles | Classification | Preset temperature | Time | Fluorescence collection |
|---|---|---|---|---|---|---|
| Preincubation | None | 1 | 1 | 95° C. | 10 min | None |
| Amplification | Quantitative analysis | 35 | Denaturation | 95° C. | 10 sec | — |
|  |  |  | Annealing | 55° C. | 10 sec | — |
|  |  |  | Expansion | 72° C. | 12 sec | Single |
| Melting curve analysis | Melting curve | 1 | Denaturation | 95° C. | 0 sec | — |
|  |  |  | Annealing | 65° C. | 15 sec | — |
|  |  |  | Melting | 95° C. 0.1° C./sec. | 0 sec | Successive |
| Cooling | None | 1 | 1 | 40° C. | 30 sec | — |

The invention is described in more detail below by way of examples and test examples. Note that the invention is not limited to the following examples.

In the following examples, seven bacteria primers (bacteria primers 5 to 11), one Spa primer and one mecA primer for MRSA (spa primer 2 and mecA primer 2), one fungi primer (Fungi primer 5), and one reference Tm value measurement primer (bacteria primer 3) were used (eleven primers in total).
Experimental Material and DNA Extraction 160 strains (preserved strains) determined to be positive among 1323 specimens collected by the Clinical Laboratory, Toyama University Hospital from Apr. 1, 2004 to Mar. 31, 2005 were used.

An automated microbial detection system ("Bact/Alert" manufactured by bioMerieux Japan Ltd.) was used for culturing.

An SA culture bottle (for aerobic bacteria), an SN culture bottle (for anaerobic bacteria), and a PF culture bottle (for detecting serious infantile disease pathogenic bacteria) were used in combination. Isolation and identification were carried out according to usual methods.

DNA was extracted as follows. The preserved strains were cultured on Mueller-Hinton agar (manufactured by Nippon Becton Dickinson Company, Ltd.), sheep blood agar (manu- Tm Value Data Analysis by Melting Curve Analysis The Tm value after real-time PCR was analyzed as follows. Specifically, the quantitative curve was checked to quantitatively determine each primer.

When the number of rising cycles of a specific primer was significantly smaller than those of other primers, it was determined that the primer was not effective.

The shape of the melting curve was then checked.

When a cliff at which the PCR product rapidly dissociated into single strands (a rapid decrease in F1 value) was not observed, the Tm value was not employed.

After checking above two items, the Tm value was calculated from the peak of the melting peak curve.
Primer Detection Sensitivity The detection sensitivity of each primer was measured in advance. The results are shown in Table 2.

TABLE 2

| Primer | Detection limit (genomic DNA) |
|---|---|
| bacteria primer 5 | 1 ng/μl |
| bacteria primer 6 | 1 fg/μl |
| bacteria primer 7 | 10 fg/μl |
| bacteria primer 8 | 1 fg/μl |

TABLE 2-continued

| Primer | Detection limit (genomic DNA) |
|---|---|
| bacteria primer 9 | 10 pg/μl |
| bacteria primer 10 | 1 ng/μl |
| bacteria primer 11 | 1 fg/μl |
| fungi primer 5 | 10 pg/μl |
| spa primer 2 | 10 pg/μl |
| mecA primer 2 | 1 ng/μl |

In order to evaluate the detection sensitivity, the genomic DNA removed from the strain was sequentially diluted, and the presence or absence of detection was checked by real-time PCR.

A difference was observed for the detection sensitivity of each primer. The sensitivity of the system was set at 1 ng/μl based on the primers with the lowest detection sensitivity (bacteria primers 5 and 10 and mecA primer 2).

Creation of Pathogenic Bacteria Tm Value Database

In order to construct a system that identifies unknown septicemia pathogenic bacteria, a Tm value database relating to pathogenic bacteria with high frequency was created.

In order to determine pathogenic bacteria registered in the database, the detection frequency was determined for the 160 strains determined to be positive in the blood culture examinations conducted by the Clinical Laboratory, Toyama University Hospital from Apr. 1, 2004 to Mar. 31, 2005, and a database was created for 34 pathogenic bacteria in total (Tables 3 to 7).

The pathogenic bacteria were classified by the items "gram positive", "gram negative", "coccus", and "*bacillus*", and listed in order from the pathogenic bacteria with the highest frequency.

These tables can be utilized as a tool for searching for the Tm value from the bacteria. A control Tm value obtained by the combination of the DNA of the *E. coli* standard strain and the bac.7 primer was set at 84.43° C.

In the tables, the Tm value in the bracket may or may not be detected.

The compilation of the symbol "(-)" and the Tm value indicate that the Tm value was not detected or indicate the detected Tm value.

The symbol "–" indicates that the Tm value was not detected.

The gram-positive cocci are shown in Table 3.

TABLE 3

| name | Fungi.5 | bac.5 | bac.6 | bac.7 | bac.8 | bac.9 | bac.10 | bac.11 | Spa.2 | mecA.2 |
|---|---|---|---|---|---|---|---|---|---|---|
| S. aureus (MRSA) | — | 82.94 | 82.39 | 82.39 | 83.87 | 80.66 | 81.51 | 80.87 | 81.07 | −76.21 |
| S. epidermidis (MRSE) | — | 83.22 | 82.33 | 83.05 | 83.7 | 80.87 | 81.47 | 80.3 | — | −75.88 |
| Staphylococcus capitis. Subsp. ureolyticus | — | 83.78 | 82.5 | 83.05 | 83.75 | 80.77 | 81.43 | 81.17 | — | −76.13 |
| S. capitis. Subsp. capitis | — | 83.65 | 82.37 | 83.1 | 83.64 | 80.12 | 81.31 | 80.24 | — | — |
| Staphylococcus auricularis | — | 83.18 | 82.57 | 83.14 | 83.87 | 80.56 | 81.86 | 80.96 | 81.9 | −76.14 |
| Staphylococcus warneri | — | 83.49 | 82.16 | 83.11 | 84.2 | 80.5 | 81.66 | 81.55 | — | — |
| Staphylococcus hominis | — | 83.05 | 82.92 | 83 | 83.77 | 79.87 | 81.44 | 80.79 | — | — |
| Streptococcus bovis | — | 82.75 | 83.2 | 82.8 | 84.3 | 79.53 | 80.84 | 82.58 | — | — |
| Streptococcus mitis | — | 83.36 | 82.6 | 82.93 | 83.36 | 81.6 | 81.43 | 83.31 | — | — |
| Streptococcus oralis | — | 83.42 | 82.65 | 82.83 | 83.47 | 81.91 | 81.43 | 83.37 | — | — |
| Streptococcus pneumoniae | — | 83.47 | 82.42 | 83 | 83.26 | 81.27 | 81.2 | 83.1 | — | — |
| Enterococcus faecalis | — | 84.75 | 82.78 | 84.2 | 84.24 | 80.71 | 82.16 | 83.63 | — | — |
| Enterococcus faecium | — | (-) 84.28 | 82.14 | 83.96 | 83.97 | 81.36 | 81.32 | 83.06 | — | — |
| Enterococcus avium | — | (-) 83.87 | 81.88 | 83.85 | 84.02 | 81.22 | 81.76 | 82.66 | — | — |
| Enterococcus gallinarum | — | 83.67 | 82.1 | 84.08 | 84.2 | (-) 81.22 | 81.9 | 82.17 | — | — |

The gram-positive bacilli are shown in Table 4.

TABLE 4

| name | Fungi.5 | bac.5 | bac.6 | bac.7 | bac.8 | bac.9 | bac.10 | bac.11 | Spa.2 | mecA.2 |
|---|---|---|---|---|---|---|---|---|---|---|
| Corynebacterium species | — | 85.33 | 85.86 | 84.76 | (-) 84.27 | 81.82 | 84.41 | 84.18 | — | — |
| Listeria monocytogenes | — | 84.44 | 81.74 | 84.27 | 83.71 | 81.46 | 81.95 | 81.77 | — | — |
| Bacillus cereus | — | 84.02 | 83.21 | 83.4 | 83.3 | 81.3 | 81.49 | 82.15 | — | — |

TABLE 5

| name | Fungi.5 | bac.5 | bac.6 | bac.7 | bac.8 | bac.9 | bac.10 | bac.11 | Spa.2 | mecA.2 |
|---|---|---|---|---|---|---|---|---|---|---|
| Acinetobacter species | — | 84.11 | 82.65 | 82.4 | 83.47 | 80.26 | (-) 80.63 | 81.88 | — | — |

The gram-negative cocci are shown in Table 5.
The gram-negative bacilli are shown in Table 6.

TABLE 6

| name | Fungi.5 | bac.5 | bac.6 | bac.7 | bac.8 | bac.9 | bac.10 | bac.11 | Spa.2 | mecA.2 |
|---|---|---|---|---|---|---|---|---|---|---|
| *Escherichia coli* | — | 84.62 | 83.76 | 84.6 | 85.06 | 81.5 | 83.03 | 82.64 | — | — |
| *Klebsiella pneumoniae* | — | 85.02 | 84.48 | 84.85 | 84.29 | 81.2 | 81.84 | 81.14 | — | — |
| *Klebsiella oxytoca* | — | 84.84 | 83.46 | 84.43 | 83.84 | 81.08 | 81.42 | 81.21 | — | — |
| *Pseudomonas aeruginosa* | — | 84.59 | 82.49 | 83.53 | 83.94 | 81.52 | (-) 83.14 | 82.96 | — | — |
| *Enterobacter cloacae* | — | 84.85 | 84.39 | 84.84 | 84.27 | 81.41 | 81.81 | 81.15 | — | — |
| *Enterobacter aerogenes* | — | 84.71 | 83.36 | 84.78 | 84.74 | 80.74 | 82.46 | 81.16 | — | — |
| *Haemophilus influenzae* | — | 84.01 | 82.34 | 82.85 | 83.36 | 80.65 | 81.58 | 81.81 | — | — |
| *Citrobacter freundii* | — | 85.03 | 84.14 | 84.96 | 84.91 | 81.12 | 82.32 | 81.75 | — | — |
| *Morganella morganii* | — | 84.42 | 83.38 | 83.94 | 84.54 | 80.9 | 82.8 | 81.46 | — | — |
| *Sphingomanas paucimobilis* | — | — | 83.06 | 83.47 | 83.56 | 81.87 | 81.67 | 83.58 | — | — |
| *Serratia marcescens* | — | 84.76 | 83.82 | 84.27 | 84.01 | 80.92 | 82.48 | 81.65 | — | — |
| *Kluyvera ascorbata* | — | 83.7 | 82.41 | 83.27 | 83.89 | 80.85 | 81.84 | 80.67 | — | — |

The fungi are shown in Table 7.

TABLE 7

| name | Fungi.5 | bac.5 | bac.6 | bac.7 | bac.8 | bac.9 | bac.10 | bac.11 | Spa.2 | mecA.2 |
|---|---|---|---|---|---|---|---|---|---|---|
| *Candida albicans* | 79.79 | — | — | — | — | — | — | — | — | — |
| *Candida krusei* | 81.11 | — | — | — | — | — | — | — | — | — |
| *Candida parapsilosis* | 79.62 | — | — | — | — | — | — | — | — | — |

Creation of Pathogenic Bacteria Identification Chart

When analyzing unknown septicemia pathogenic bacteria, one control Tm value and ten PCR amplification product Tm values are obtained. The database shown in Tables 3 to 7 is inconvenient for identifying pathogenic bacteria from the Tm values.

Therefore, a pathogenic bacteria identification chart was created in order to easily identify pathogenic bacteria from the Tm values (Table 8).

TABLE 8

| fungi.5 | spa.2 | bac.5 | bac.6 | bac.7 | bac.8 | bac.9 | bac.10 | bac.11 | mecA.2 | name |
|---|---|---|---|---|---|---|---|---|---|---|
| 81.11 | — | — | — | — | — | — | — | — | — | *Candida krusei* |
| 79.79 | — | — | — | — | — | — | — | — | — | *Candida albicans* |
| 79.62 | — | — | — | — | — | — | — | — | — | *Candida parapsilosis* |
| — | 81.9 | 83.18 | 82.57 | 83.14 | 83.87 | 80.56 | 81.86 | 80.96 | −76.14 | *Staphylococcus auricularis* |
| | | | −0.61 | 0.57 | 0.73 | −3.31 | 1.3 | −0.9 | | |
| — | 81.07 | 82.94 | 82.39 | 82.39 | 83.87 | 80.66 | 81.51 | 80.87 | −76.21 | *S. aureus* (MRSA) |
| | | | −0.55 | 0 | 1.48 | −3.21 | 0.85 | −0.64 | | |
| — | — | 85.33 | 85.86 | 84.76 | (-) 84.27 | 81.82 | 84.41 | 84.18 | — | *Corynebacterium* species |
| | | | 0.53 | −1.1 | −0.49 | −2.45 | 2.59 | −0.23 | | |
| — | — | 85.03 | 84.14 | 84.96 | 84.91 | 81.12 | 82.32 | 81.75 | — | *Citrobacter freundii* |
| | | | −0.89 | 0.82 | −0.05 | −3.79 | 1.2 | −0.57 | | |
| — | — | 85.02 | 84.48 | 84.85 | 84.29 | 81.2 | 81.84 | 81.14 | — | *Klebsiella pneumoniae* |
| | | | −0.54 | 0.37 | −0.56 | −3.09 | 0.64 | −0.7 | | |
| — | — | 84.85 | 84.39 | 84.84 | 84.27 | 81.41 | 81.81 | 81.15 | — | *Enterobacter cloacae* |
| | | | −0.46 | 0.45 | −0.57 | −2.86 | 0.4 | −0.66 | | |
| — | — | 84.84 | 83.46 | 84.43 | 83.84 | 81.08 | 81.42 | 81.21 | — | *Klebsiella oxytoca* |
| | | | −1.38 | 0.97 | −0.59 | −2.76 | 0.34 | −0.21 | | |
| — | — | 84.76 | 83.82 | 84.27 | 84.01 | 80.92 | 82.48 | 81.65 | — | *Serratia marcescens* |
| | | | −0.94 | 0.45 | −0.26 | −3.09 | 1.56 | −0.83 | | |
| — | — | 84.75 | 82.78 | 84.2 | 84.24 | 80.71 | 82.16 | 83.63 | — | *Enterococcus faecalis* |
| | | | −1.97 | 1.42 | 0.04 | −3.53 | 1.45 | 1.47 | | |

TABLE 8-continued

| fungi.5 | spa.2 | bac.5 | bac.6 | bac.7 | bac.8 | bac.9 | bac.10 | bac.11 | mecA.2 | name |
|---|---|---|---|---|---|---|---|---|---|---|
| — | — | 84.71 | 83.36 | 84.78 | 84.74 | 80.74 | 82.46 | 81.16 | — | Enterobacter aerogenes |
|   |   |   | −1.35 | 1.42 | −0.04 | −4 | 1.72 | −1.3 |   |   |
| — | — | 84.62 | 83.76 | 84.6 | 85.06 | 81.5 | 83.03 | 82.64 | — | Escherichia coli |
|   |   |   | −0.86 | 0.84 | 0.46 | −3.56 | 1.53 | −0.39 |   |   |
| — | — | 84.59 | 82.49 | 83.53 | 83.94 | 81.52 | (-) | 82.96 | — | Pseudomonas aeruginosa |
|   |   |   | −2.1 | 1.04 | 0.41 | −2.42 | 83.14 | −0.18 |   |   |
|   |   |   |   |   |   |   | 1.62 |   |   |   |
| — | — | 84.44 | 81.74 | 84.27 | 83.71 | 81.46 | 81.95 | 81.77 | — | Listeria monocytogenes |
|   |   |   | −2.7 | 2.53 | −0.56 | −2.25 | 0.49 | −0.18 |   |   |
| — | — | 84.42 | 83.38 | 83.94 | 84.54 | 80.9 | 82.8 | 81.46 | — | Morganella morganii |
|   |   |   | −1.04 | 0.56 | 0.6 | −3.64 | 1.9 | −1.34 |   |   |
| — | — | (-) | 82.14 | 83.96 | 83.96 | 81.36 | 81.32 | 83.06 | — | Enterococcus faecium |
|   |   | 84.28 | −2.14 | 1.82 | 0 | −2.6 | −0.04 | 1.74 |   |   |
| — | — | 84.11 | 82.65 | 82.4 | 83.47 | 80.26 | (-) | 81.88 | — | Acinetobacter species |
|   |   |   | −1.46 | −0.25 | 1.07 | −3.21 | 80.63 | 1.25 |   |   |
|   |   |   |   |   |   |   | 0.37 |   |   |   |
| — | — | 84.02 | 83.21 | 83.4 | 83.3 | 81.3 | 81.49 | 82.15 | — | Bacillus cereus |
|   |   |   | −0.81 | 0.19 | −0.1 | −2 | 0.19 | 0.66 |   |   |
| — | — | 84.01 | 82.34 | 82.85 | 83.36 | 80.65 | 81.58 | 81.81 | — | Haemophilus influenzae |
|   |   |   | −1.67 | 0.51 | 0.51 | −2.71 | 0.93 | 0.23 |   |   |
| — | — | (-) | 81.88 | 83.85 | 84.02 | 81.22 | 81.76 | 82.66 | — | Enterococcus avium |
|   |   | 83.87 | −1.99 | 1.97 | 0.17 | −2.8 | 0.54 | 0.9 |   |   |
| — | — | 83.78 | 82.5 | 83.05 | 83.75 | 80.77 | 81.43 | 81.17 | −76.13 | Staphylococcus capitis. Subsp. ureolyticus |
|   |   |   | −1.28 | 0.55 | 0.7 | −2.98 | 0.66 | −0.26 |   |   |
| — | — | 83.7 | 82.41 | 83.27 | 83.89 | 80.85 | 81.84 | 80.67 | — | Kluyvera ascorbata |
|   |   |   | −1.29 | 0.86 | 0.62 | −3.04 | 0.99 | −1.17 |   |   |
| — | — | 83.67 | 82.1 | 84.08 | 84.2 | (-) | 81.9 | 82.17 | — | Enterococcus gallinarum |
|   |   |   | −1.57 | 1.98 | 0.12 | 81.22 | 0.68 | 0.27 |   |   |
|   |   |   |   |   |   | −2.98 |   |   |   |   |
| — | — | 83.65 | 82.37 | 83.1 | 83.64 | 80.12 | 81.31 | 80.24 | — | S. capitis. Subsp. capitis |
|   |   |   | −1.28 | 0.73 | 0.54 | −3.52 | 1.19 | −1.07 |   |   |
| — | — | 83.49 | 82.16 | 83.11 | 84.2 | 80.5 | 81.66 | 81.55 | — | Staphylococcus warneri |
|   |   |   | −1.33 | 0.95 | 1.09 | −3.7 | 1.16 | −0.11 |   |   |
| — | — | 83.47 | 82.42 | 83 | 83.26 | 81.27 | 81.2 | 83.1 | — | Streptococcus pneumoniae |
|   |   |   | −1.05 | 0.58 | 0.26 | −1.99 | −0.07 | 1.9 |   |   |
| — | — | 83.42 | 82.65 | 82.83 | 83.47 | 81.91 | 81.43 | 83.37 | — | Streptococcus oralis |
|   |   |   | −0.77 | 0.18 | 0.64 | −1.56 | −0.48 | 1.94 |   |   |
| — | — | 83.36 | 82.6 | 82.93 | 83.36 | 81.6 | 81.43 | 83.31 | — | Streptococcus mitis |
|   |   |   | −0.76 | 0.33 | 0.43 | −1.76 | −0.17 | 1.88 |   |   |
| — | — | 83.22 | 82.33 | 83.05 | 83.7 | 80.87 | 81.47 | 80.3 | −75.88 | S. epidermidis (MRSE) |
|   |   |   | −0.89 | 0.72 | 0.65 | −2.83 | 0.6 | −1.17 |   |   |
| — | — | 83.05 | 82.92 | 83 | 83.77 | 79.87 | 81.44 | 80.79 | — | Staphylococcus hominis |
|   |   |   | −0.13 | 0.08 | 0.77 | −3.9 | 1.57 | −0.65 |   |   |
| — | — | 82.75 | 83.2 | 82.8 | 84.3 | 79.53 | 80.84 | 82.58 | — | Streptococcus bovis |
|   |   |   | 0.45 | −0.4 | 1.5 | −4.77 | 1.31 | 1.74 |   |   |
| — | — | — | 83.06 | 83.47 | 83.56 | 81.87 | 81.67 | 83.58 | — | Sphingomanas paucimobilis |
|   |   |   |   | 0.41 | 0.09 | −1.69 | −0.2 | 1.91 |   |   |

* Control Tm value = 84.43o C.

The Tm value in the bracket may or may not be detected.

The compilation of the symbol "(-)" and the Tm value indicate that the Tm value was not detected or indicate the detected Tm value.

The symbol "—" indicates that the Tm value was not detected.

The value provided under each Tm value indicates the difference from the Tm value in the left column.

The items are checked from the leftmost item. Fungi for which the Fungi primer was positive are determined with the highest priority.

The item "spa" follows the item "fungi.5" since the number of bacteria for which spa is positive is small.

The item "mecA" is given the lowest priority because the presence or absence of a methicillin resistant gene differs even if the bacterial species is the same.

*Staphylococcus epidermidis* and some other *Staphylococcus* species may have mecA. However, the item "mecA" is given the lowest priority so that identification does not become complicated when mecA is negative. Regarding the identification method excluding the above-mentioned items, a combination of the Tm values using the seven bacteria primers is analyzed.

The primers are arranged in order from the primer (bac.5) with the highest Tm value.

This facilitates the search process.

The differential value was also provided to indicate the bacteria Tm value differential pattern. The positive or negative difference from the Tm value in the left column is indicated by the symbol "±". This enables a determination based on the difference pattern of the seven bacteria Tm values without being affected by a measurement error of the real-time PCR instrument corresponding to each measurement cycle.

Verification by Blind Test

Test 1

In order to evaluate the system according to the invention, real-time PCR was performed using the eleven primer sets according to the invention while concealing the bacterium names. The combination of the Tm values was compared with the database to identify the bacterial species.

Table 9 shows the combination of the resulting Tm values.

TABLE 9

| Fungi.5 | Spa.2 | bac.5 | bac.6 | bac.7 | bac.8 | bac.9 | bac.10 | bac.11 | mecA.2 | name |
|---|---|---|---|---|---|---|---|---|---|---|
| — | — | 84.17 | 82.05 | 83.09 | 83.46 | 81.03 | 82.7 | 82.56 | — | ? |
|  |  |  | −2.12 | 1.04 | 0.37 | −2.43 | 1.67 | −0.14 |  |  |

Fungi5, spa2, and mecA2 were negative, and the Tm values of the PCR product were obtained for only the bacteria primers.

Since the control Tm value was 84.02, it was determined that an error of −0.41 occurred from the original value (84.43). Therefore, corrections were made by adding +0.41 to the Tm value for Bac.5.

Since the Tm value for bac.5 was 84.58, the range from 84.78 to 84.28 in the pathogenic bacteria chart was selected (Bac.5 column in Table 10) taking an instrument error of ±0.2° C. into consideration.

Since the difference in Tm value between Bac.5 and Bac.6 is −2.12° C., the difference in the range from −1.92 to −2.32 was selected taking an instrument error of ±0.2° C. into consideration. As a result, *Enterococcus faecalis*, *Pseudomonas aeruginosa*, and *Enterococcus faecium* remained as candidates.

Since the difference in Tm value between Bac.6 and Bac.7 was +1.04, only *Pseudomonas aeruginosa* remained by focusing on the range from +1.24 to +0.84.

The differences in Tm value regarding bac.8, 9, 10, and 11 coincided with the database values of *Pseudomonas aeruginosa*.

As a result of twelve blind tests, correct identification results could be obtained for all the tests.

See TABLE 10 (page 22).

Convenient Alternative Method that does not Utilize Tm Value

It is possible to easily and rapidly identify whether pathogenic bacteria are bacteria, fungi, or MRSA using the primers according to the invention without using a Tm value measurement instrument such as a real-time PCR instrument.

Figure 1:
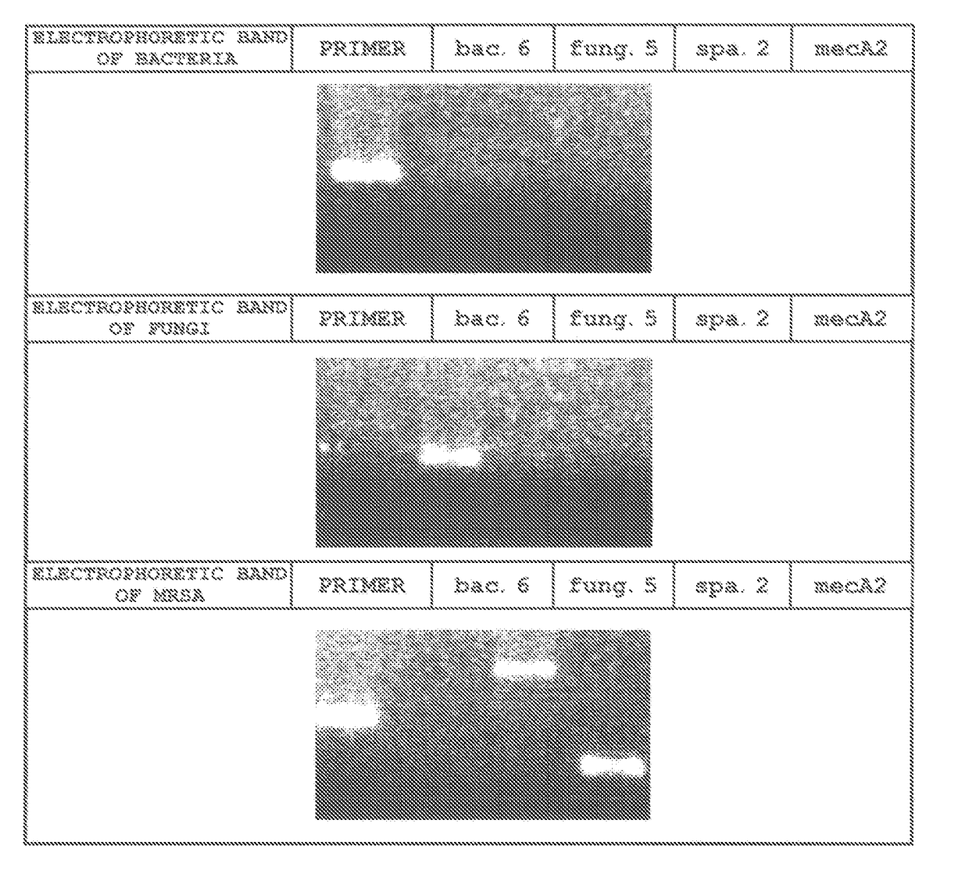
FIG. 1 shows an agarose gel electrophoresis band.

Specifically, the DNA of unknown pathogenic bacteria as a template is subjected to PCR using a PCR thermal cycler utilizing one bacteria primer, one fungi primer, one Spa primer, and one mecA primer according to the invention, and the amplification product is subjected to agarose gel electrophoresis. If a band with a known size is observed, infections due to bacteria, fungi, and MRSA can be distinguished (FIG. 1).

As a result, infections due to bacteria, fungi, and MRSA can be easily and rapidly distinguished even in a facility without a real-time PCR instrument and the like so that an appropriate antimicrobial drug can be selected at an early stage.

TABLE 10

| fungi.5 | spa.2 | bac.5 | bac.6 | bac.7 | bac.8 | bac.9 | bac.10 | bac.11 | mecA.2 | name |
|---|---|---|---|---|---|---|---|---|---|---|
| — | — | 84.76 | 83.82 | 84.27 | 84.01 | 80.92 | 82.48 | 81.65 | — | *Serratia marcescens* |
|  |  |  | −0.94 | 0.45 | −0.26 | −3.09 | 1.56 | −0.83 |  |  |
| — | — | 84.75 | 82.78 | 84.2 | 84.24 | 80.71 | 82.16 | 83.63 | — | *Enterococcus faecalis* |
|  |  |  | −1.97 | 1.42 | 0.04 | −3.53 | 1.45 | 1.47 |  |  |
| — | — | 84.71 | 83.36 | 84.78 | 84.74 | 80.74 | 82.46 | 81.16 | — | *Enterobacter aerogenes* |
|  |  |  | −1.35 | 1.42 | −0.04 | −4 | 1.72 | −1.3 |  |  |
| — | — | 84.62 | 83.76 | 84.6 | 85.06 | 81.5 | 83.03 | 82.64 | — | *Escherichia coli* |
|  |  |  | −0.86 | 0.84 | 0.46 | −3.56 | 1.53 | −0.39 |  |  |
| — | — | 84.59 | 82.49 | 83.53 | 83.94 | 81.52 | (-) | 82.96 | — | *Pseudomonas aeruginosa* |
|  |  |  | −2.1 | 1.04 | 0.41 | −2.42 | 83.14 | −0.18 |  |  |
|  |  |  |  |  |  |  | 1.62 |  |  |  |
| — | — | 84.44 | 81.74 | 84.27 | 83.71 | 81.46 | 81.95 | 81.77 | — | *Listeria monocytogenes* |
|  |  |  | −2.7 | 2.53 | −0.56 | −2.25 | 0.49 | −0.18 |  |  |
| — | — | 84.42 | 83.38 | 83.94 | 84.54 | 80.9 | 82.8 | 81.46 | — | *Morganella morganii* |
|  |  |  | −1.04 | 0.56 | 0.6 | −3.64 | 1.9 | −1.34 |  |  |
| — | — | (-) | 82.14 | 83.96 | 83.96 | 81.36 | 81.32 | 83.06 | — | *Enterococcus faecium* |
|  |  | 84.28 | −2.14 | 1.82 | 0 | −2.6 | −0.04 | 1.74 |  |  |

Since the bacteria primer used in the invention reacts with the DNA of all bacteria, it is necessary to use high-purity DNA polymerase in which mixing of the DNA of bacteria originating from the recombinant host is minimized.

FIG. 1 shows an agarose gel electrophoresis band determined using the above convenient alternative method.

Primers used: bac.6, fungi.5, spa, and mecA

DNA polymerase used: AmpliTaq Gold DNA Polymerase, LD (manufactured by Applied Biosystems)

Pathogenic bacteria responsible for infection (particularly septicemia) can be rapidly detected and identified using the method according to the invention so that a rapid septicemia diagnosis method is implemented.

Specifically, since the invention enables construction of a system that identifies pathogenic bacteria within two hours, an optimum antimicrobial drug can be selected at an early stage of septicemia.

Moreover, a therapeutic effect after administration of an antimicrobial drug can be monitored.

What is claimed is:

1. A method for identifying pathogenic microorganism responsible for infection, the method comprising:
performing gene amplification using one or more of specific primer sets Fungi 1 to Fungi 7 that specifically amplify a gene region common to 18S rRNA genes of fungi to obtain Tm values of the gene region of fungi;
performing gene amplification using a specific primer set (spa or spa2) and (mecA or mecA2) that specifically amplifies the Spa gene and the mecA gene of methicillia resistant *staphlococcus aureus* to obtain Tm values of the Spa gene and the mecA gene;
amplifying a gene region of a 16S rRNA gene of bacteria that includes a base sequence region common to bacteria using three or more primer sets including a first primer set, a second primer set, and a third primer set among specific primer sets Bac.1 to Bac.11 to obtain a combination of Tm values of the gene region of known bacteria;
storing the Tm values of the gene region of the fungi, the Spa gene, the mecA gene, and the gene region of the known bacteria in a database;
subjecting the DNA of an unknown microorganism to gene amplification using the primer sets used to create the database; and
selecting known bacteria presumed to be included within an error range of a measured value and a measurement instrument based on the Tm values obtained using the first primer set from the database when it is proved that the unknown microorganism is bacteria based on a combination of Tm values of a specific gene region that has been determined to be positive, the specific gene region having been determined to be negative when being amplified by the specific primer set (spa or spa2) and (mecA or mecA2), and
sequentially narrowing a range of the known bacteria included within the error range of the measurement instrument based on the Tm values obtained using the second primer set and the third primer set to identify the unknown microorganism.

2. The method according to claim 1, further comprising measuring a reference Tm value of a standard strain in each cycle using the primer sets used to create the database, and correcting an error of the measurement instrument using the reference Tm value.

3. The method according to claim 1, further comprising identifying the unknown microorganism based on a combination of differences between the Tm values obtained using the three or more primer sets including the first primer set, the second primer set, and the third primer set.

4. The method according to claim 1, the gene amplification being performed by real-time PCR.

5. A method for identifying pathogenic microorganism responsible for infection, the method comprising:
performing gene amplification using one or more of specific primer sets Bac.1 to Bac.11 that specifically amplify a gene region common to the 16S rRNA gene of bacteria to obtain Tm values of the gene region of bacteria;
performing gene amplification using a specific primer set (spa or spa2) and (mecA or mecA2) that specifically amplifies the Spa gene and the mecA gene of methicillia resistant *staphlococcus aureus* to obtain Tm values of the Spa gene and the mecA gene;
amplifying a gene region of a 18S rRNA gene of fungi that includes a base sequence region common to fungi using three or more primer sets including a first primer set, a second primer set, and a third primer set among specific primer sets Fungi 1 to Fungi 7 to obtain a combination of Tm values of the gene region of known fungi;
storing the Tm values of the gene region of the bacteria, the Spa gene, the mecA gene, and the gene region of the known fungi in a database;
subjecting the DNA of an unknown microorganism to gene amplification using the primer sets used to create the database; and
selecting known fungi presumed to be included within an error range of a measured value and a measurement instrument based on the Tm values obtained using the first primer set from the database when it is proved that the unknown microorganism is fungi based on a combination of Tm values of a specific gene region that has been determined to be positive, and
sequentially narrowing a range of the known fungi included within the error range of the measurement instrument based on the Tm values obtained using the second primer set and the third primer set to identify the unknown microorganism.

6. The method according to claim 5, further comprising measuring a reference Tm value of a standard strain in each cycle using the primer sets used to create the database, and correcting an error of the measurement instrument using the reference Tm value.

7. The method according to claim 5, further comprising identifying the unknown microorganism based on a combination of differences between the Tm values obtained using the three or more primer sets including the first primer set, the second primer set, and the third primer set.

8. The method according to claim 5, the gene amplification being performed by real-time PCR.

* * * * *